United States Patent
Rueb et al.

(10) Patent No.: US 6,170,111 B1
(45) Date of Patent: Jan. 9, 2001

(54) TEETH-CLEANING DEVICE WITH A HANDLE

(75) Inventors: Fritz Alfons Rueb; Fritz Walter Rueb, both of Schönau (DE)

(73) Assignee: Rueb Holding GmbH, Schönau (DE)

( * ) Notice: Under 35 U.S.C. 154(b), the term of this patent shall be extended for 0 days.

(21) Appl. No.: 09/358,034

(22) Filed: Jul. 21, 1999

Related U.S. Application Data

(63) Continuation of application No. PCT/EP98/00173, filed on Jan. 14, 1998.

(30) Foreign Application Priority Data

Jan. 21, 1997 (DE) .............................................. 197 01 891

(51) Int. Cl.⁷ ....................................................... A46B 9/04
(52) U.S. Cl. ........................... 15/106; 15/167.1; 15/176.4
(58) Field of Search ................................... 15/106, 167.1, 15/176.1, 176.4, 176.5, 176.6; D4/104

(56) References Cited

U.S. PATENT DOCUMENTS

| | | | |
|---|---|---|---|
| 2,624,062 | * | 1/1953 | Knoderer . |
| 4,319,377 | * | 3/1982 | Tarrson et al. . |
| 4,751,761 | * | 6/1988 | Breitschmid ........................ 15/176.5 |
| 4,780,923 | | 11/1988 | Schultheiss . |
| 5,005,246 | * | 4/1991 | Yen-Hui . |
| 5,029,358 | * | 7/1991 | Zimmerman ........................... 15/106 |
| 5,293,661 | * | 3/1994 | Appleby . |
| 5,313,684 | * | 5/1994 | Fitjer . |
| 5,331,708 | * | 7/1994 | Ponzini . |
| 5,435,033 | * | 7/1995 | Millner . |
| 5,758,382 | * | 6/1998 | Maekawa et al. ................... 15/176.5 |

FOREIGN PATENT DOCUMENTS

| | | | |
|---|---|---|---|
| 1 247 311 | 12/1988 | (CA) . | |
| 672 723 A5 | 12/1989 | (CH) . | |
| 42 23 196 A1 | 1/1994 | (DE) . | |
| 0 001 044 A1 | 3/1979 | (EP) . | |
| 0 256 440 | 2/1988 | (EP) . | |
| 0 441 597 A1 | 8/1991 | (EP) . | |
| 0 311 937 B1 | 4/1992 | (EP) . | |
| 0 537 663 A1 | 4/1993 | (EP) . | |
| 0 550 818 A1 | 7/1993 | (EP) . | |
| 2067894 | * 8/1981 | (GB) ................................. 15/176.1 |

* cited by examiner

Primary Examiner—Terrence R. Till
(74) Attorney, Agent, or Firm—Akin, Gump, Strauss, Hauer & Feld, L.L.P.

(57) ABSTRACT

A teeth-cleaning device (1) has a handle (2) which on one end, preferably on two opposite ends, has an interdental treatment element, for example in the form of a fine brush (3) or hard brush (4) and possibly even in the shape of a tooth pick. The treatment element is positioned perpendicular to, and projects from the longitudinal axis of the handle (2), and is removably and replaceably attached by means of a locking element (5) which can be detachably fixed in a locking position. To this end, the treatment element or a holding device forming part thereof, such as a retaining wire (4a), is inserted in the operating position into a hole (6) extending perpendicular to the longitudinal axis of the handle (2). When the locking element (5) clears this hole (6), the treatment element can be removed and a different one inserted. In the locking position, in contrast, the locking element (5) covers the hole (6) and thus prevents the removal of the treatment element inserted into the hole.

24 Claims, 6 Drawing Sheets

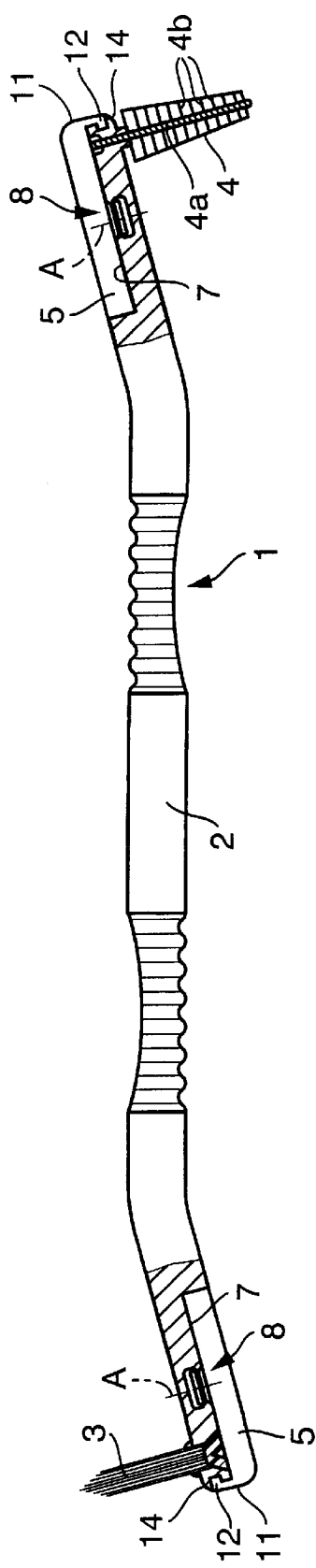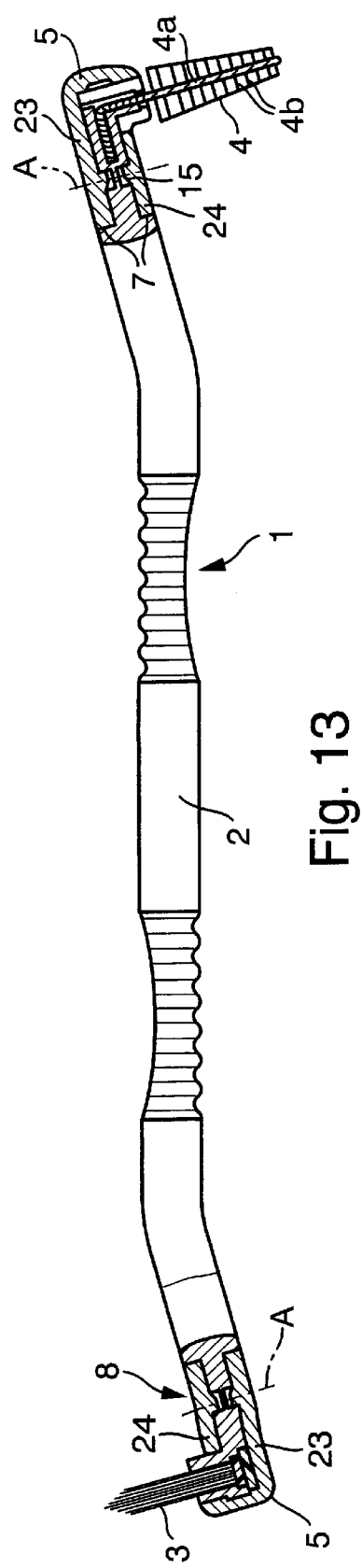

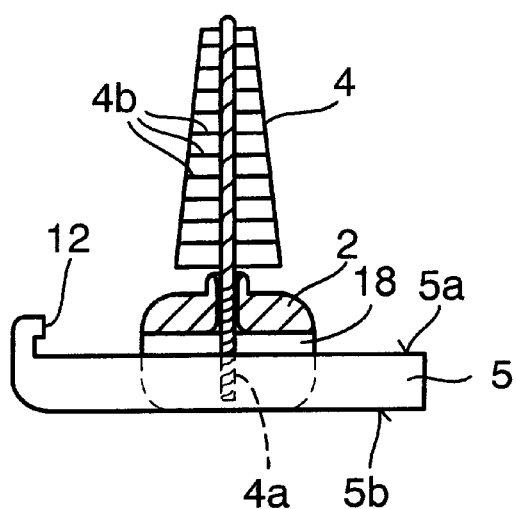
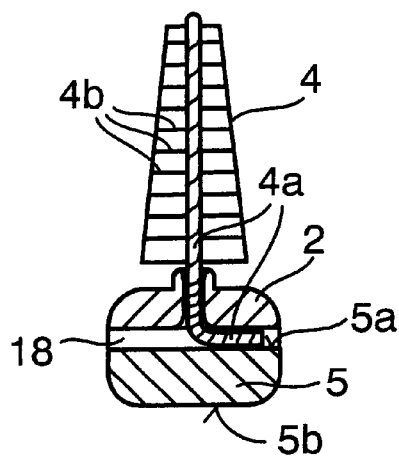
Fig. 6
Fig. 7
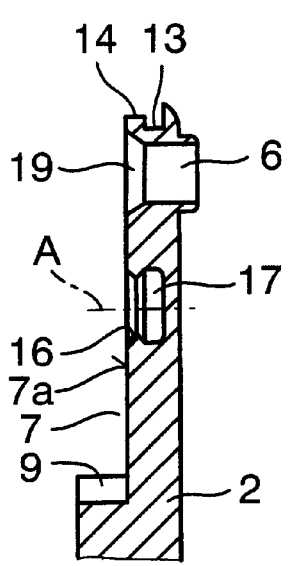
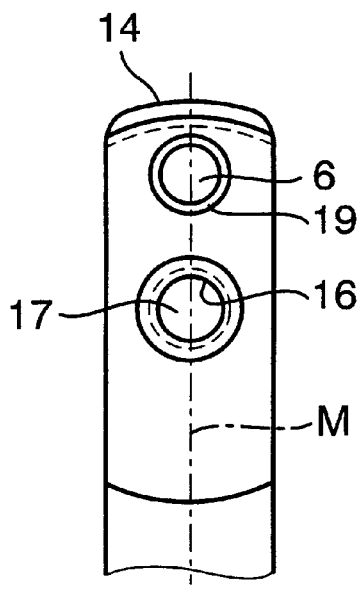
Fig. 8
Fig. 9

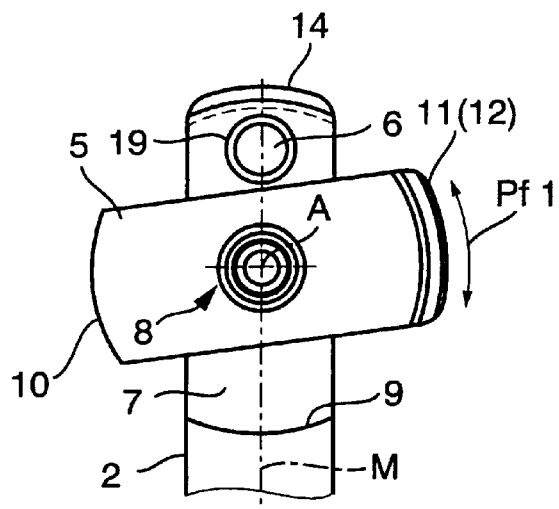
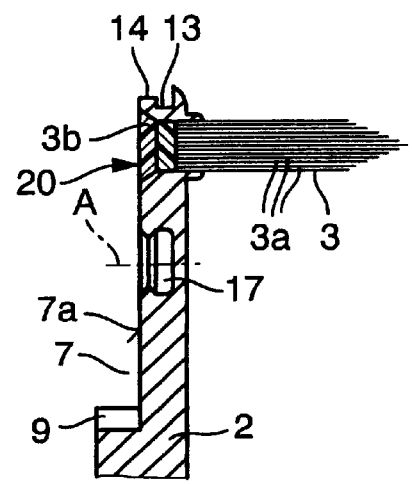
Fig. 10  Fig. 11
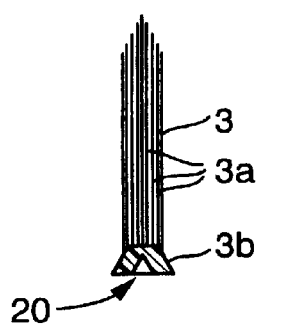
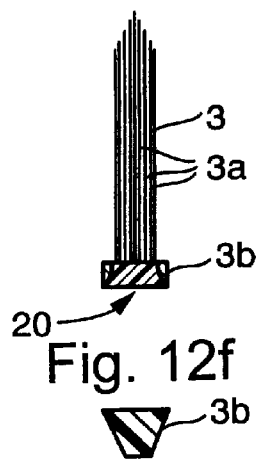
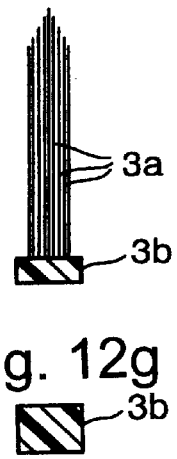
Fig. 12a  Fig. 12f  Fig. 12g
Fig. 12b  Fig. 12c

TEETH-CLEANING DEVICE WITH A HANDLE

CROSS REFERENCE TO RELATED APPLICATION

This application is a continuation of International Application PCT/EP98/00173, filed Jan. 14, 1998, the disclosure of which is incorporated herein by reference.

BACKGROUND OF THE INVENTION

The invention concerns a teeth-cleaning device with a handle and at least one interdental treatment element in the form of, for example, a soft brush and/or a hard brush and/or a toothpick, which treatment element is provided on the handle protruding transversely to its longitudinal extension, in a detachable and exchangeable manner, and in the operating position is locked by means of a lock which can be fastened in a locked position, wherein the treatment element or one retaining device associated with it in the operating position passes through the hole which extends transversely to the handle and the treatment element or its retaining device in the case of an open lock, when it exposes the cross-section of the hole, can be inserted into the hole and, furthermore, wherein in the closed position the lock overlaps the hole and prevents the removal of the treatment element.

Such a teeth-cleaning device is known from EP-O 311 937 B1. In this case the treatment element is a cylindrical or tapered hard brush, where the bristles are held by a twisted wire which can be anchored as a retaining element in a hole of the handle with a lock. In this case the lock is a slide which can be displaced transversely to the central axis of the treatment element and coaxially to the end of the handle, the lock having an opening on the face, with which a retaining plate of the treatment element can be engaged in the locked position. At the same time, the slide is constructed as a sleeve and for the purpose of replacing the treatment element it can be pushed in the direction of the handle away from its end. Therefore the pushing movement to open this lock is against that direction with which the handle and the treatment element are introduced into the mouth and possibly in the region of the molar teeth, so that there will be a danger that during the insertion the sleeve can be moved unintentionally into the open position. Therefore during the cleaning of the interdental region, i.e. the region between two teeth, which is often not simple to clean, the lock can open and the treatment element can become detached from its retaining device. This can even result in injuries in the oral cavity.

From U.S. Pat. No. 4,780,923 a teeth-cleaning device of the type mentioned in the introduction is known, wherein a pivoting flap is used as a lock, the pivot axis of which is provided on the outermost end of the handle on the face in such a manner that the hole for retaining the treatment element is oriented more towards the center of the handle. At the same time, the pivot axis is oriented transversely or perpendicularly to the extension of the handle and to the extension of the central axis of the treatment element. In the closed position, this flap-shaped lock is supposed to be locked relative to the end of the handle by virtue of the design of its cross-section, while laterally protruding flanges are provided to seize the opening and closing movements.

In this case too, there is the danger that, for example, if one slips during the cleaning of the interdental region, especially of the molar teeth, these actuating flanges will come to rest against the edge of the teeth or the like in such a manner that the lock could open unintentionally. Moreover, the manufacture of the parts which fit each other and interlock with each other and their joining with a transversely extending axis is relatively complicated. In addition, when closing this pivoting lock the retaining wire of the brush-shaped treatment element is bent over in the same direction in which this lock is folded for the purpose of closing, so that the lock is also under the tension of this retaining device of the treatment element, the tension acting in the direction of opening.

From EP-A-0 537 663 A1 a teeth-cleaning device of the same kind is known, wherein as treatment element an approximately cylindrical brush with a central retaining wire is provided, while the retaining wire is anchored as a retaining device in a hole of the handle. In the initial position, this wire passes through a hole and protrudes past the handle on that side which is averted from the brush. As a lock a slide is used which can be displaced transversely to this wire and coaxially towards the end of the handle, which slide with a stop is first at a greater distance to the face of the handle and then is pushed onto this handle. At the same time its rearward portion acts on the protruding portion of the retaining wire and bends it while being pushed on. Although by virtue of this the direction of pushing approximately agrees with the load during the introduction of the teeth-cleaning device into the mouth, it is, however, not ruled out that during the cleaning movements the lock is pushed inadvertently back again into the open position.

From DE-A-42 23 196 A1 a brush holder for a toothbrush is known, which also has a lock, which during the locking process is moved perpendicularly to the longitudinal axis of the treatment element. At the same time, the lock is provided pivotably on a recess, into which a retaining wire for the bristles can be inserted. In the region of this recess this retaining wire is deformed and is axially secured by the lock by pivoting it into the closed position. Apart from the elaborate construction of the actual brush holder and the mounting of this lock, with an actuating end it faces the actual brush holder so that it could be opened again. Thus an unintentional opening cannot be ruled out.

SUMMARY OF THE INVENTION

Therefore, an object of the invention is to produce a teeth-cleaning device of the type mentioned in the introduction, which is simpler to produce and has a lock, with which the danger of an unintentional opening, especially in the mouth and during use, is excluded as far as possible.

To achieve this objective the teeth-cleaning device mentioned in the introduction is characterized in that the lock has a slat-shaped construction and is provided in a recess or a reduced cross-section of the handle in such a manner that in the locked or operating position it is flush with or is a protrusion-free component of the handle, and that this lock has a rotary mounting on the handle which is spaced from the hole for the treatment element, the axis of the rotary mounting extending parallel to the longitudinal axis of the treatment element.

Thus, when the cleaning of the teeth is carried out, the lock is oriented and secured in the longitudinal direction of the handle and for the purpose of opening it has to be rotated about the axis extending parallel to the treatment element and thus transversely to the handle, which is a rotating or pivoting movement practically not occuring during use, so that an unintentional opening of the lock during the cleaning process is practically ruled out. Since at the same time the lock extends protrusion-free and is flush with the handle, there are no projections present which could result in or lead to an unintentional opening movement during the cleaning process.

A sleeve as a lock, which would have to be produced separately, is avoided as is a flap-shaped lock partly overlapping and surrounding the end region of the handle, which requires laterally protruding flanges or protrusions for its actuation. Nonetheless, the lock according to the invention can be well grasped and rotated, since its entire length is available for holding and grasping and the entire lock can be rotated or pivoted for its actuation similarly to a clamp handle.

The recess of the handle to accommodate the slat-shaped lock can be provided on that side of the handle which is averted from the protruding handling element and is flat, at least partly, wherein this flat can extend past the hole, and the side of the slat-shaped lock facing this flat is also flat and level. By virtue of this the lock can slide over this surface of the recess or along this surface very closely when it is rotated to be opened or closed. The locking effect with regard the treatment element is equally good, since it is correspondingly reliably fixed and secured in the closed position.

Particularly advantageous is when the lock clamps a portion or region of the treatment element in the locked position. This results not only in the fixing of the lock itself, but also in a better anchoring of the treatment element, so that this too can well absorb and transmit the forces occurring during the treatment.

The external side of the lock, which faces away from the hole and the treatment element, in the operating position can be aligned in height and width with the remaining surface of the handle and in the locked position the lock can complement the cross-section of the recess of the handle. This provides a particularly convenient design of the slat-shaped or handle-shaped lock which is flush with the handle and is protrusion-free, thus not presenting any interference to the user in the mouth during the cleaning process and not providing any point of application of force for unintentional adjusting movements.

For a good overlapping of the hole contained in the handle and thus for a good locking of the treatment element, it is advantageous if the hole for accommodating and retaining the treatment element is closer to the end of the handle than the rotary mounting of the lock. The lock can well protrude past the rotary mounting towards the end of the handle and pivot about it to the side for the purpose of replacing the treatment element.

Particularly advantageous is if the lock has two arms or sections extending in opposite directions from the rotary mounting, one of which engages or overlaps the hole in the locked position and the other extends from the rotary mounting in the direction of the handle up to a shoulder bounding the recess. At the same time both these sections may have the same lengths, so that the user has a lock which is easy to manipulate, can be rotated about its center similarly to a turn handle or clamp handle to bring it to its various end positions. Moreover, this provides better and more possibilities to lock the lock, in particular in the locked position for the clamping and/or snapping in, thus preventing unintentional opening movements. The shoulder between the handle and the recess may be provided approximately perpendicularly to the longitudinal extension of the handle and in the transverse direction can have particularly a concave curvature, and the face of the lock facing this shoulder in the locked position may have a corresponding concave curvature, wherein the radius of curvature corresponds to the distance of this face to the axis of the rotary mounting. Thus, when the lock is pivoted or rotated into the locked position during the last portion of its movement, it is guided not only by the rotary mounting but also by the contact between its face and the shoulder of the recess. Moreover, the lock in the longitudinal direction of the shoulder obtains an additional support, when the shoulder and the face are in contact in the locked position, possibly in a clamped manner, to better ensure the locked position.

A device to fix the locked position by means of a frictional or clamping force and/or form-locking and/or snapping-in may be provided at least on one side of the lock, possibly on its underside. In this manner a plurality of individual possibilities, which may also be used in combination, are produced for the fixing of the lock in the locked position. This is made possible above all by the shape according to the invention and the direction of movement of the lock within a recess. A useful construction of the fixing of the lock may be that on that face of the lock which faces toward the recess a protrusion is provided for a clamped and/or snapped-in fixing of the lock in the locked position. This protrusion could be, for example, constructed on the handle itself as a shoulder above the recess. Even more advantageous is when the protrusion is provided on the face of the lock itself and it overlaps and/or engages the edge of the handle on its end face in the locked position, in particular by frictional locking or by snapping-in on the end of the handle. In this manner, in the locked position the lock can contact the handle in the axial direction at both its ends and be actively connected with it, which relieves not only its rotary mounting, but results also in an appropriately secure mounting and fixing of this locked position, especially because in this position the lock fits the recess flush and protrusion-free with the rest of the handle and thus does not offer practically any point of application for forces to be exerted on it while cleaning the teeth. Retaining means may be also provided on that face of the lock which faces the shoulder and/or on this shoulder for a detachable fastening of the locked position, in particular by clamping and/or by snapping-in. This can complement the fixing provided on the opposite end of the lock or be used instead of it to fix the lock in the operating and locked position.

As rotary mounting of the lock, a mushroom-shaped protrusion may be provided on the handle as one part, and on the counterpart a recess may be provided which snaps-in with this mushroom-shaped protrusion and surrounds the mushroom head with a collar or a protrusion, whereby the mushroom-shaped protrusion may be provided especially on the lock and the recess on the handle, although it may be vice versa. However, as far as manufacture and assembly are concerned, it is more convenient if the mushroom-shaped protrusion is provided on the lock and it can be pressed into a corresponding cutout in the recess of the handle.

In a teeth-cleaning device with a replaceable hard brush, the bristles of which are held by a central, particularly a twisted wire, according to the design of the invention it is particularly useful if the retaining wire passes through the hole of the handle in the region of the recess and protrudes past the hole within the reach of the rotating lock and can be bent over relative to the hole by turning the lock into its closed position. The protrusion of the wire is to be so chosen on this occasion, that in this unbent position it does not protrude past the external contour of the handle and of the lock. Accordingly, in this case the twisting effects simultaneously the form-locked fixing of the treatment element, while the wire to be bent additionally clamps the lock in its closed position or at least contributes to its fixing, which may be carried out additionally by further means and measures in accordance with the constructions described above.

At the same time for a good retention of the hard brush and its retaining wire, it is advantageous if on that side of the recess which faces the lock a groove is provided to accommodate the retaining wire bent over by the lock, which groove extends transversely to the longitudinal extension of the handle and its axis of curvature coincides with the axis of the rotary mounting, and if the hole for the purpose of passing through the retaining wire opens into this groove, especially to the bottom of the groove. In this manner the underside of the lock can abut against the upper side of the recess of the handle and be guided in it, so that the rotary mounting retains the best position to be able to be turned and the retaining wire can still be bent over and held in the bent-over state since in this case it is accommodated in the said groove, the cross-section of which is equal to or greater than the cross-section of the retaining wire and, consequently, can accommodate it. At the same time the tensioning of the retaining wire results in a certain frictional locking between the retaining wire and the lock.

In the case of a teeth-cleaning device of the type according to the invention with a fine brush-shaped treatment element, which consists of a bundle of approximately parallel bristles, which at that end which is opposite to the treating end is joined by welding and/or by the retaining plate, the radial expansion of the retaining plate can overlap the cross-section of the bundle of bristles, and the bundle of bristles can be inserted through a hole accommodating the retaining plate in a form-locking manner, while in the entry region, which faces away from the exit of the bristles, the hole has a widening which corresponds to the shape and size of the retaining plate and the retaining plate is approximately flush with the edge of the hole when this treatment element is in the operating position. In the locked position the lock can abut against or be close to the surface of the retaining plate, particularly under pressure. Thus, this treatment element constructed as a bundle of bristles or soft brush is prevented, i.e., securely fixed, from falling through the hole due to its radial expansion in the region of the retaining plate and from being pushed out from it by the lock moved into the locked position. At the same time, the lock can interact with the upper side of the retaining plate, which faces away from the bristles, in the sense of a clamping. However, the lock can also be fixed in its locked position in the above described manner.

The retaining plate may have an approximately oval, circular or polygonal outline or external contour and a semi-spherical, plate-shaped and longitudinal section tapering in particular in the direction of the bristles, which fits the correspondingly shaped widening of the retaining hole of the handle and is held therein in the axial direction. Accordingly, this retaining plate has a twin function, whereby on the one hand it holds together the bristles and on the other contributes to the fixing of the treatment part in the hole and to the form-locking.

A very considerable and advantageous significance in the construction of the teeth-cleaning device can be that the handle has a treatment element at least in two places, particularly two different treatment elements, in particular at the opposite situated end regions, each of which is held detachably and in a replaceable manner in the operating position by a rotating lock according to the invention. Thus the user has several possibilities without the need of exchanging the treatment elements. However, he can discard each treatment element after its use or wear, for example.

At the same time, it is convenient if both treatment elements protrude on the opposite situated ends of the shaft or handle in opposite situated sides from the shaft or the handle transversely to its longitudinal extension. In this manner a treatment element, not being used, does not hinder the user, since during the introduction of a treatment element into the mouth it is directed practically in the opposite direction, i.e., away from the user.

At the same time, it is convenient if at one end a pointed fine brush formed from a bundle of bristles is provided and at the other end a hard brush with a retaining wire and bristles protruding from it. Thus the user can enjoy simultaneously the advantages of both of these treatment elements.

A very special design or development of the invention which is worth protecting on its own may be that the length of the hole, extending on the handle transversely to its longitudinal extension, is divided for at least one treatment element in such a manner that one portion of the internal wall of the hole is provided on the handle and the portion of the internal wall complementing it in the operating position is provided on the lock or on a leg of this lock, which leg extends approximately parallel to the axis of rotation of the lock, and that in the case of an open lock, for the purpose of inserting the treatment element or a retaining device associated with it, the hole is divided and exposed and after pivoting or rotating the lock into the locked position it surrounds the treatment element or the retaining device of the treatment element.

Therefore when the lock is open, the hole is divided, and it is laterally accessible, so that the treatment element or its retaining device does not have to be inserted into this hole in its full length but can be inserted somewhat parallel to itself laterally into the hole or its open portion, after which the lock is pivoted into the locked position and consequently the hole is complemented and closed laterally, thus surrounding and fixing the treatment element or a retaining device of a treatment element. This will considerably facilitate and simultaneously improve the insertion or the exchange of a treatment element, since an even better fit of the hole with regard to the retaining device or the treatment element is achieved due to the better access. Moreover, the lock obtains an additional function by virtue of containing a portion of the hole which is closed by its locked position.

A particularly advantageous development can be achieved wherein the divided hole has a widening or a groove which extends in particular in the direction of the rotary mounting of the lock, which groove can be enclosed by the lock, to accommodate a retaining wire bent over in this region. Into the extension, which is divided just like the hole, a head of the treatment element can be inserted and fixed by locking the lock, whereas a retaining wire can be pushed into the groove or riffle, the wire is then bent over so that its further extension together with the hard brush carried by it will be perpendicular to the handle. In this case the lock will lock again at least that part of the hole which is perpendicular to the handle. At the same time, the groove or riffle can be in the hole or orifice situated in the longitudinal central plane of the handle, which hole or orifice is independent from the lock but can be enclosed by it.

Above all, such a lock, which has a portion of the hole and with this portion complements the hole in the closed position, makes a stability-improving construction feasible in such a manner that this lock has two, approximately slat-shaped parts which are parallel to each other, which are rotatably mounted on parallel flats of the handle, that the region or leg of the lock containing a portion of the hole joins both slat-shaped portions and that the entire lock has an approximately U-shaped longitudinal section, whereby the two slat-shaped portions form the legs of the U and contain the rotary mounting. Accordingly, in contrast to a lock formed only by one slat-shaped part, such a lock is produced which, above all, surrounds in the closed position the corresponding retaining end of the handle on both sides and by virtue of this can produce a considerably more stable retention, mounting and stronger locking action. Thus a simple mounting is produced for the treatment element or a retention of a treatment element and yet a very secure retention for it.

Altogether, when combining single or several of the features and steps described above a teeth-cleaning device is produced, on which hard brushes and/or soft brushes are secured without elaborate sleeves, and yet they can be fastened on the handle in a replaceable manner without making the handle disproportionately expensive due to elaborate mechanisms. At the same time a good maneuverability is produced, as well as a simple and safe actuation and fixing of the slat-shaped or U-shaped lock, which can be used as a clamp handle or pivoting hook, in particular by interacting with a snap-in mechanism which prevents a rotation or pivoting of this lock during the cleaning process. Since the width of the lock in the region of its mounting corresponds to the width of the handle, and the lock is matched also to suit a recess of the handle accommodating it with regard to its other cross-sectional and longitudinal sectional contour, and accordingly is flush and aligned with it, injuries in the mouth during the treatment due to protruding actuating protrusions or the like are avoided. Such protrusions for the actuation of the lock are, however, unnecessary, because due to its slat-shape and its transverse extension relative to its rotary mounting the lock can be used as a turn handle.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that the invention is not limited to the precise arrangements and instrumentalities shown. In the drawings, partially schematically illustrated:

FIG. 1 is a teeth-cleaning device according to the invention, in side view, partially longitudinally sectioned, which at both of its end regions has treatment elements projecting approximately perpendicularly in opposite directions, which treatment elements are each held by a lock locked in its operating position;

FIG. 6 is a cross-section of the handle in the region of a hole, into which a retaining wire of an interdental treatment element, constructed as a hard brush, is inserted, wherein the lock is rotated to the open position and the retaining wire protrudes in the movement region of this lock;

FIG. 7 is an illustration corresponding to FIG. 6, with the lock, being now in the closed position, also cross-sectioned, wherein as a result of the closing movement the protrusion of the retaining wire is bent over and is deformed in a groove for the retaining wire, which groove extends next to the hole;

FIG. 8 is an illustration corresponding to FIG. 2 of the end region of the handle of a teeth-cleaning device according to the invention with a larger hole for a modified treatment element;

FIG. 9 is a top view corresponding to FIG. 3 of the recess in the end region of the handle;

FIG. 10 is a top view of the end region according to FIG. 9 with a lock snapped in on the recess by the rotary mounting, in the open position;

FIG. 11 is an illustration corresponding to FIG. 8 after the insertion of a treatment element, constructed as a soft brush which has a plurality of parallel bristles fixed on a retaining plate;

FIGS. 12a to 12i illustrates several embodiments, modifications of FIG. 11, of an approximately soft brush-shaped treatment element with a retaining plate for the bristle and for the fixing in the handle, wherein the side views of these treatment elements and partial top views on the retaining plates are illustrated collectively in FIGS. 12a to 12i;

FIG. 13 is a side view of a teeth-cleaning device, partially longitudinally sectioned, similar to that of FIG. 1, wherein the locks are modifications of those shown in FIG. 1;

DETAILED DESCRIPTION OF THE INVENTION

Figure 2:
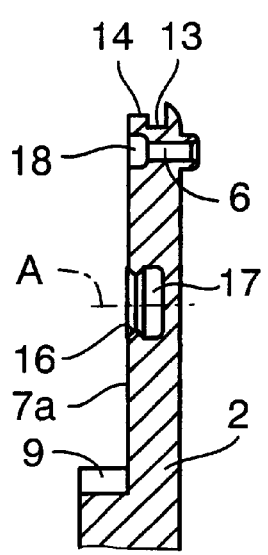
FIG. 2 is a longitudinal section through the end of the handle of the teeth-cleaning device according to the invention in side view with the recess for a rotating lock, yet without this lock.

In the following description concurring parts or those having the same function have concurring reference numerals even if their design or shape is slightly different.

A teeth-cleaning device, designated in toto by 1, has an approximately shaft-shaped handle 2 with grasping aids and, in the embodiments according to FIG. 1 and FIG. 13, has at both ends an interdental treatment element 3 and 4 in the form of a fine brush 3 consisting of a bristle brush with essentially parallel single bristles 3a and a retaining plate 3b combining them at one end, and at the other end a hard brush 4 having a twisted retaining wire 4a and bristles 4b held and protruding approximately radially or laterally from it. It is also conceivable to replace one of these treatment elements by a toothpick, since these treatment elements, which are provided on the handle 2 transversely to its longitudinal extension in a protruding manner, are fastened in a detachable and replaceable manner and in the operating position are locked by means of a lock 5 which can be secured in the locked position and will be described later in the following.

Figure 14:
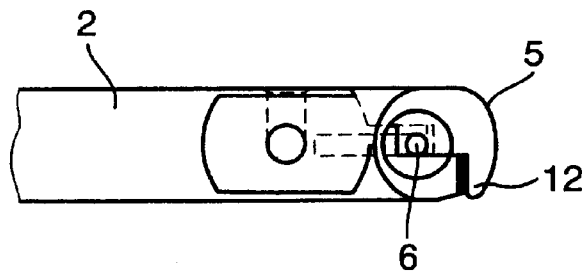
FIG. 14 is a view of one of the ends of the teeth-cleaning device according to FIG. 13, wherein the treatment element is not yet inserted but the lock is closed.
Figure 15:
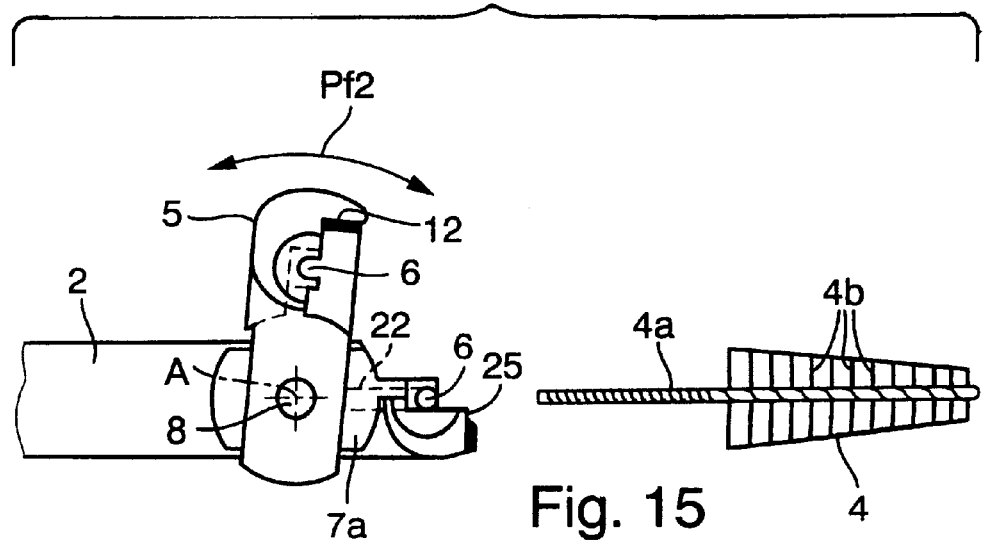
FIG. 15 is an illustration corresponding to FIG. 14, wherein the lock is pivoted to the open position and a treatment element constructed as a hard brush with a retaining wire is illustrated prior to the insertion into a horizontal hole and bending over into a divided hole, situated partially in the lock.
Figure 16:
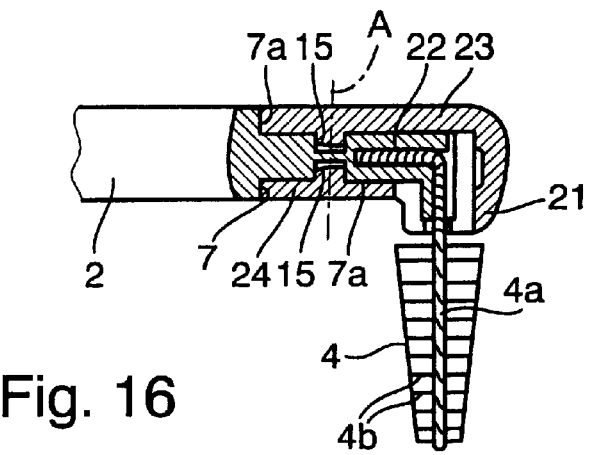
FIG. 16 is a longitudinal section through the end of a teeth-cleaning device illustrated in FIGS. 14 and 15, after the insertion of the treatment element illustrated in FIG. 15 and after the pivoting of the lock into the closed position, wherein it can be seen that the lock has two parallel slat-shaped parts with an aligned rotary mounting and a hole, extending transversely to the handle of the teeth-cleaning device; is provided partly in the handle and partly in the lock and at the same time allocated to a leg extending transversely to the slat-shaped parts.
Figure 17:
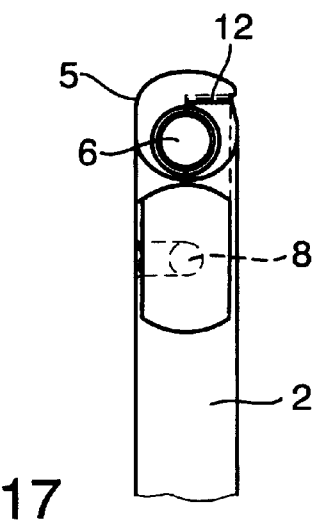
FIG. 17 is a top view corresponding to FIG. 14 of the other end of the treatment element illustrated in FIG. 13, wherein the lock is closed without a treatment element having been inserted.
Figure 18:
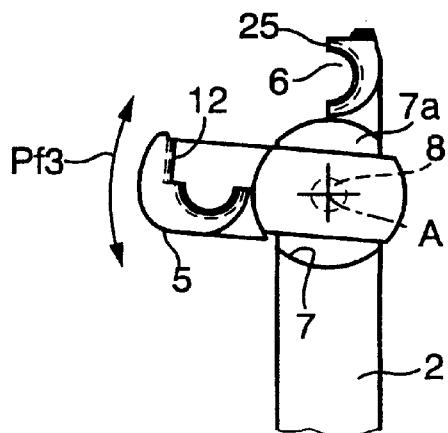
FIG. 18 is a view of one end of the teeth-cleaning device corresponding to FIG. 17, wherein the lock, which has a U-shape in the longitudinal section in this case also, is open and consequently the hole to accommodate the treatment element, provided partly in the handle and partly in this lock, is also open and divided.
Figure 19:
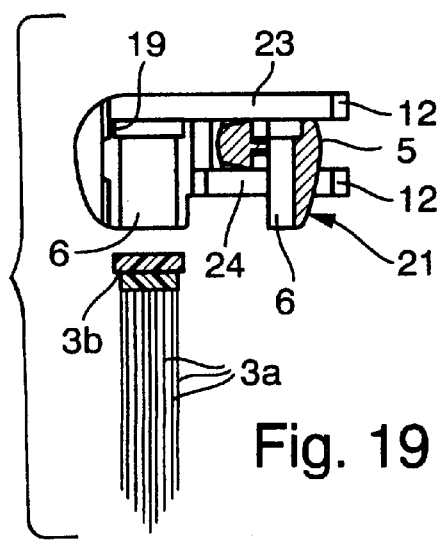
FIG. 19 is a front view of the end of the teeth-cleaning device and of the handle illustrated in FIG. 18 with the lock open and prior to inserting a treatment element constructed as a soft brush.
Figure 20:
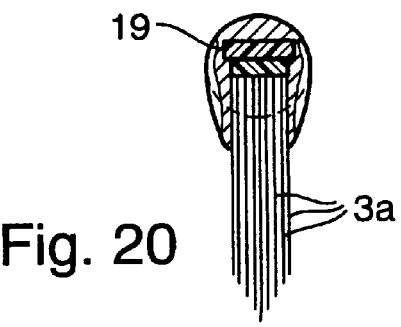
FIG. 20 is a cross-section of the end of the teeth-cleaning device with inserted treatment element, constructed as a soft brush.

In the FIGS. 2, 6 and 7 on the one hand and in FIGS. 8 and 11 on the other, furthermore in FIGS. 15 and 16 on the one hand and in FIGS. 18 to 20 on the other, one can recognize that the respective treatment element 3 or one of the retaining devices associated with it, e.g., the retaining wire 4a of the hard brush 4, passes through a hole 6 which extends transversely to the handle 2, the cross-section of which corresponds, of course, to the part to be accommodated, whereas the hole 6 in FIGS. 2 and 8 is still empty, while the respective treatment element is inserted into it in FIGS. 6 and 7 on one hand and into FIG. 11 on the other, whereas in the case of the embodiments according to FIGS. 13 to 20 the respective hole 6 is divided in a manner yet to be described, and its wall parts are partly on the handle 2 and partly on the correspondingly constructed lock 5.

At the same time, the respective treatment element 3 or 4 or its retaining device, in the case of an open lock 5 according to FIGS. 6 and 10, when the lock exposes the cross-section of the hole 6 and its entrance, can be inserted into this hole, so that the arrangement according to FIGS. 6 or 11 will occur. In the closed position according to FIG. 7 and additionally to FIG. 1 the lock 5 covers the respective hole 6 and thus prevents the removal of the treatment element; in other words, it fixes the treatment element by virtue of its closed position. When it is moved back to the open position, the treatment element can be removed and replaced or exchanged.

One can see, especially based on FIGS. 4 to 7 and 10 as well as on FIG. 1, that the lock 5 has a slat-shaped design and is arranged in a recess 7, i.e., in a reduction of the cross-section of the handle 2, in such a manner that in the locked and operating position according to FIGS. 1 and 7 it is a flush and protrusion-free component of the handle 2 as far as the cross-section is concerned. In addition, the figures show that at a distance from the hole 6 this lock 5 has a rotary mounting 8 for the treatment element provided on the handle 2, the axis A of the rotary mounting extending approximately parallel to the longitudinal axis of the respective treatment element. This makes a rotation according to the double arrow Pf 1 in FIG. 10 feasible, so that by virtue of its different length and width, the slat-shaped lock 5 can be so rotated that it exposes the hole 6 or, when rotated to the locking position according to FIGS. 1 and 7, it covers the hole and in this locked position it complements the handle 2 in this end region, consequently has no protruding projections or actuating flanges or the like. In an advantageous manner such grasping aids are not required on the lock 5, since it itself can be grasped and moved as a twist handle.

The recess 7 of the handle 2 to accommodate the lock 5 is provided on that side of the handle 2 which is averted from the treatment element, i.e., the fine brush 3 and the hard brush 4, and at the same time is flat on the side of the lock 5. This flattening 7a extends past the hole 6 and the side or underside 5a (cf. FIGS. 5 and 6) of the slat-shaped lock 5 facing this flattening 7a is also flat, so that the facing flat sides of the recess 7 and of the lock 5 lie against each other in the operating position, as this can be seen, for example, in FIG. 7, while even a reciprocal frictional contact may be provided for the detachable fastening of the lock 5.

In any case, in the locked position the lock 5 acts in a clamping manner on a part or region of the recess 7 or, possibly, even the treatment element, as this is shown for example in FIG. 7, whereby the retaining wire 4a is bent over and held down by the lock 5 in the locked position, so that a certain reciprocal holding action occurs between these parts.

Especially from FIG. 1 will it become clear that the height and width of the external side 5b of the lock 5, which faces away from the hole 6 and the treatment element, is aligned with the surface of the handle 2, and the surface of the handle extends without any protrusion, so that in the locked position the lock 5 complements in the recess 7 the cross-section of the handle 2 and thus just fills the recess 7.

At the same time the hole 6, to accommodate and retain the treatment element, is closer to the end of the handle 2 than the rotary mounting 8 of the lock 5. The result of this is clearly illustrated in FIG. 10, where the lock 5 can be rotated to a transverse position relative to the handle 2 thus exposing the hole 6 for the purpose of replacing the treatment element. On the same occasion, in the open position the lock 5 protrudes only laterally relative to the handle 2 and does not extend it in this open position.

From FIG. 10 (in which the lock is illustrated transparently to some extent and thus its rotary mounting 8 is also visible) it will also be clear that the lock 5 has two arms extending in opposite directions from its rotary mounting 8, one of which overlaps the hole 6 in the locked position and the other extends from the rotary mounting 8 in the direction of the handle 2 up to the shoulder 9 which bounds the recess 7. This shoulder 9 between the handle 2 and the recess 7, which bounds the recess 7 towards the center of the handle also, is somewhat perpendicular to the longitudinal extension and, according to FIGS. 3, 9 and 10, has a concave curvature in the transverse direction, in fact symmetrically to the longitudinal central plane M of the handle 2. According to FIGS. 4 and 10, the face 10 of the lock 5, which in the locked position faces this shoulder 9, has a corresponding and essentially conforming convexly curved radius, while the radius of curvature corresponds to the distance of this face 10 from the axis A of the rotary mounting 8, so that in the last phase of the closing movement of the lock and in the first phase of its opening movement the face 10 is guided by the shoulder 9 in a sliding manner and, possibly, a certain frictional force needs to be overcome. The shoulder 9 and the face 10 can, namely, contact each other in the locked position, possibly by jamming, consequently contributing to the fixing of the locked position.

On the face 11 of the lock 5, which is on the side opposing the shoulder 9 and the face 10, in the embodiment there is a hook-like protrusion 12 provided which extends practically over the entire face 11 and is curved in this direction also, for the purpose of clamping and/or fixing the lock 5 in the locked position. At the same time, this protrusion 12 could engage the face 11 of the lock 5, but in the embodiment is provided on and moulded onto the face 11 of the lock itself and in the locked position overlaps or engages the edge 14 on the end face of the handle 2 with a slot-shaped groove 13 with the corresponding curvature (see especially FIGS. 2, 8 and 11). Above all this contact between the protrusion 12 and the edge 14 or the groove 13 can be a frictionally-locking one and take place possibly by snapping-in and thus the lock 5 can be fixed detachably in the closed position. At the same time, this fixing may be sufficient on its own or may interact with the mentioned additional frictional and clamping forces. For example, retaining means, frictional lock for example, may be provided on that side 10 of the lock 5 which faces the shoulder 9 and/or on this shoulder 9, for the purpose of a detachable fixing of the locked position.

In addition, a stop may be provided, resulting in a limitation of the pivoting movement of the lock in its locking position, so that it could be opened in one direction only and in the opposite direction could not be pivoted past its locked position. On the other hand, this could be prevented by the user himself, on the basis of aligning the dimensions between the lock 5 and the handle 2, noting and setting the exact locked position when determining the locked position.

Figure 5:
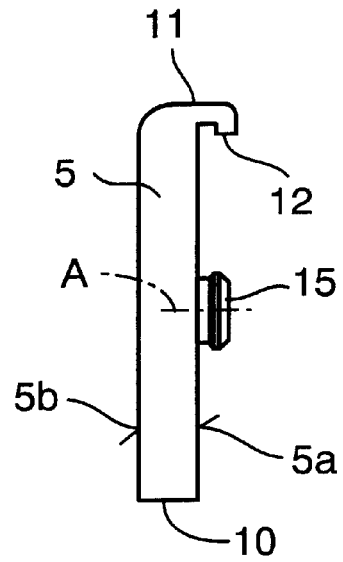
FIG. 5 is a side view of the lock according to FIG. 4 with a mushroom-shaped protrusion provided on it for the purpose of interacting with a corresponding socket opening, visible in FIG. 2, by means of which a rotary mounting for the lock is formed.
Figure 12H:
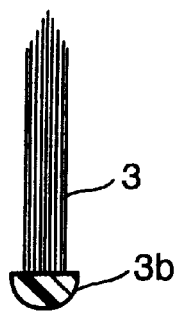
Figure 12I:
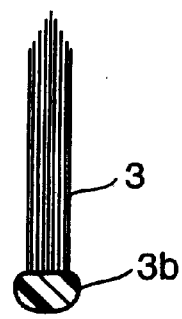
Figure 12D:
Figure 12E:

To realize the already mentioned rotary mounting 8 on one of the parts which can be rotated relative to each other, a mushroom-shaped protrusion 15 and on the counterpart a recess 17 is provided which with a collar 16 or a protrusion engages from behind this mushroom-shaped protrusion 15 and the mushroom head in a snap-in manner, wherein in FIG. 5 the mushroom-shaped protrusion 15 and in FIGS. 2, 8 and 11 the correspondingly shaped recess 17 can be clearly recognized. In the embodiment the mushroom-shaped protrusion 15 is provided on the lock 5 and the recess 17 on the handle 2 inside the recess 7.

It is illustrated in FIGS. 6 and 7, that a treatment element constructed as a replaceable hard brush 4 can be used, wherein the bristles 4b are held by the central retaining wire 4a and protrude from this approximately in the radial direction. At the same time, the retaining wire 4a passes through the correspondingly tight hole 6 of the handle 2 (in the region of the recess 7) and according to FIG. 6 protrudes past the hole 6 in the region of the rotatable lock 5. Thus, according to FIG. 7, by rotating the lock 5 into its locked position, the retaining wire can be bent over relative to the hole 6 and consequently fixed. Therefore the user can insert this hard brush 4 by means of its retaining wire 4a into the hole 6 up to the stop and then close the lock, thus automatically fixing the hard brush, since the protrusion of the retaining wire 4a is deformed to a hook-like shape.

Figure 3:
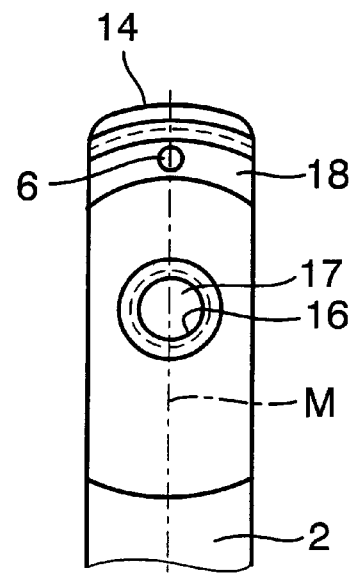
FIG. 3 is a top view of the recess in the end region of the handle of the teeth-cleaning device according to FIG. 2.
Figure 4:
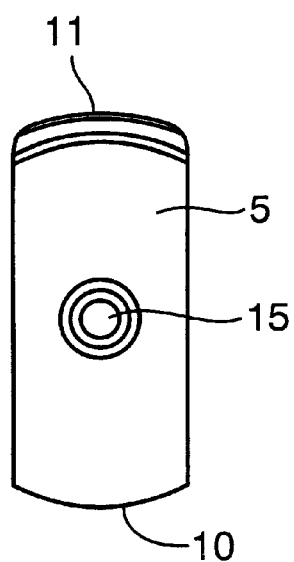
FIG. 4 is a top view of a slat-shaped lock, the width of which corresponds to the width of the recess in the end region of the handle and fits into the recess.

On this occasion the recess 7, on that side 7a which is facing the lock 5 and its underside 5a, has a groove 18 extending transversely to the longitudinal extension of the handle 2 (having a curvature with the axis A of the rotary mounting 8 as its center) to accommodate the retaining wire 4a bent over by the lock 5, while the hole 6 for the purpose of pushing through the retaining wire 4a into this groove 18 opens to the bottom of the groove, a fact which will be particularly clear when considering FIGS. 2 and 3. The protrusion of the retaining wire 4a is therefore bent over in a groove 18 which is dimensioned accordingly, so that the underside 5a of the lock 5 can abut against the upper side 7a of the recess 7, although the protrusion of the retaining wire 4a is to be accommodated between the lock 5 and the handle 2. At the same time, the bending forces of the retaining wire 4a can contribute to the detachable fixing of the lock, as due to this an additional clamping or an increased frictional force can act directly on the retaining wire 4a on the one hand, and on the rotary mounting 8 on the other.

FIG. 11 shows the fixing of a treatment element constructed as a fine brush 3, wherein single bristles 3a are combined by means of a retaining plate 3b. At the same time, one can recognize, especially in FIG. 11, that the radial expansion of the retaining plate 3b is greater than the cross-section of the bundle of bristles or of the fine brush 3 and the bundle of bristles is pushed through the hole 6 accommodating the retaining plate 3b in a form-locking manner and dimensioned accordingly, whereby in this case the hole 6 has in the entry region, which faces away from the exit of the bristles 3a, a widening 19 corresponding to the shape and size of the retaining plate 3b, which can be easily recognized in FIG. 8. According to FIG. 11, in the operating position the retaining plate 3b is approximately flush with the edge of the hole or the edge of this widening 19, 50 that the underside 5a of the lock 5 can be easily moved over it. Accordingly, in the locked position the lock 5 can abut against the surface 20 of the retaining plate 3b which faces away from the bristles 3b, possibly even under a slight pressure, to affect a good fastening of the fine brush 3 and to facilitate or promote simultaneously a mutual clamping and fixing in the locked position.

FIGS. 12b to 12i show that the retaining plate 3b may have an approximately oval (FIGS. 12e and 12i), circular (FIGS. 12d and 12h) or polygonal, e.g., rectangular (FIGS. 12c and 12g) or trapezoidal (FIGS. 12b and 12f) outline or external contour and at the same time a semi-spherical, plate-shaped and particularly tapering longitudinal section, which fits into the correspondingly shaped widening 19 of the retaining hole 6 of the handle 2 and results in a fastening of the fine brush 3 in the axial direction. Therefore, in the case of a closed lock 5, the fine brush 3 is fixed in both axially opposed directions, but can be pulled out from the hole 6 with the lock 5 in the open position.

It has already been explained, that the handle 2 according to FIG. 1 has in two places, namely in opposite situated end regions, a treatment element each which is different, which can be held in a detachable and exchangeable manner in the operating position by a rotating lock 5 in accordance with the above description. Both treatment elements at the opposing ends of the shaft or handle 2 of the teeth-cleaning device are protruding from this shaft or handle 2 in opposing direction. At the same time these end regions with the treatment elements are slightly bent at an obtuse angle relative to the general direction of extension of the handle 2. On one end a pointed fine brush 3, formed from a bundle of bristles, is provided and on the other end a hard brush 4 with a retaining wire 4a and bristles 4b held by and protruding from it, and accordingly the user has a plurality of possibilities to clean the interdental spaces.

In the case of the already disclosed teeth-cleaning device 1 according to the FIGS. 13 to 20 an even more stable lock and firmer fastening of the treatment elements, i.e., of a hard brush 4 (FIGS. 14 to 16) and of a fine brush 3 (FIGS. 17 to 20) is provided. At the same time, the handling during the insertion or replacement of the treatment elements is also simple or even simplified.

This is achieved by the hole 6 for the respective treatment element being divided in its length and a portion of the internal wall of the hole 6 being provided on the handle 2, and the portion of the internal wall of this hole, which complements it in the operating position, is provided on the lock 5 and in particular on a leg 21 which extends parallel to the axis of rotation A of the rotary mounting 8 of this lock 5. It becomes clear, especially from FIGS. 15, 18 and 19, that by virtue of this, when the lock 5 is open, the hole 6 will be divided and exposed for the insertion of the treatment element or a retaining device associated with it and after pivoting or turning the lock 5 to the closed position (FIGS. 14 and 16 and FIGS. 17 and 20) it surrounds the treatment element or the retaining device of a treatment element.

According to FIGS. 19 and 20 the divided hole 6 has a widening 19 and according to FIGS. 14 to 16 it has a hole 22 extending in the direction of the rotary mounting 8 of the lock 5 or a groove which can be closed by the lock 5 to accommodate a retaining wire 4b bent over in this region. According to FIG. 15 a hard brush 4 with a retaining wire 4b can be pushed first into this hole 22 in the longitudinal direction of the handle 2. Afterwards the retaining wire 4b is bent over, so that the position illustrated in FIG. 16 is assumed, wherein the portion carrying directly the hard brush 4 will rest against the handle 2 transversely to the handle's longitudinal extension, as this is shown in the embodiments according to FIGS. 1 and 7. This portion is then held in the hole 6, which, in accordance with the double arrow Pf 2 in FIG. 15, after the pivoting of the lock 5 is brought into the closed position and thus closes the hole 6 on the sides and upwards.

According to FIGS. 17 to 20, the widening 19 and the hole 6 to accommodate a treatment element constructed as a fine brush 3 are closed off in the same manner, whereby in this case the lock can be pivoted into the closing position according to the double arrow Pf 3, after a corresponding fine brush 3 had been introduced in a form-locking manner, so that it assumes the position illustrated in FIG. 20. In the case of an open lock, the fine brush 3 with its retaining plate 3b needs to be inserted only laterally into the portion of the hole 6 situated in the handle 2, whereby it is moved at right angle to itself into this portion of the hole 6, the lock is subsequently closed and consequently the fine brush 3 is fastened. Therefore the brush does not have to be inserted through the hole which was the case in the previously described embodiment.

In this embodiment according to FIGS. 13 to 20 the lock 5 has two, approximately slat-shaped parts 23 and 24 which are parallel with each other and are rotatably mounted on parallel flats 7a of the recesses 7 of the handle 2. The region or leg 21 of the lock 5 featuring a portion of the hole 6 joins these two slat-shaped parts 23 and 24 and imparts in this case to the entire lock 5 an approximately U-shaped longitudinal section, which can be easily seen in FIG. 16 as well as in FIG. 19. On this occasion the two slat-shaped parts 23 and 24 form the U-legs of this U-shaped longitudinal section, while the joining leg 21 may be considered as the central part of the U, wherein in an advantageous manner it overlaps that slat-shaped part 24 on the side of which the respective treatment element protrudes, so that the treatment element is guided and held over a greater length. The rotary mounting 8 is provided on the slat-shaped parts 23 and 24, i.e., on the U-legs of this lock 5, which can be seen particularly in FIG. 16, where corresponding protrusions 15 of the slat-shaped parts 23 and 24 engage corresponding opposite directed and aligned mounting orifices of the flats 7a of the recesses 7, 50 that they have a common axis of rotation A.

The portion of the hole 6, which is part of the handle 2, is provided to retain both a fine brush 3 and a hard brush 4 on the face of the handle 2 in such a manner, that when the lock 5 is closed the center of the hole is in the longitudinal central plane of the rotary mounting 8 of the lock 5 also. Thus an extremely symmetrical arrangement of the treatment element is achieved in its locked position.

Especially in FIG. 18 can it be seen that the separating plane of the hole 6 to accommodate the fine brush 3 corresponds to the longitudinal central plane through the rotary mounting 8 and the axis of rotation A as well as through the closed hole 6. Therefore the fine brush 3 can be inserted laterally into the hole portion which is part of the handle 2, followed by folding or pivoting the lock 5 into the closed position, thus surrounding and fixing this fine brush 3 and its retaining plate 3b in a form-locking manner. Thus the insertion or the replacement of such a fine brush 3 is very simple.

For the purpose of accommodating the retaining wire 4b of the hard brush 4, that portion of the hole 6 which is provided on the face of the handle 2 extends on both sides of the longitudinal central plane and is open on the face facing away from this; in other words, during its insertion the retaining wire 4b is moved in this longitudinal central plane. On this occasion this portion of the hole; which is situated in the handle 2, extends over more than half of the cross-section of the hole, and that portion of the hole which is situated in the lock 5 is open over its length in the direction of rotation and also extends over more than half of the cross-section of the hole, so that in the closed position a mutual overlapping is achieved while leaving the hole 6 itself exposed. This is very useful to accommodate the relatively slim retaining wire 4b and allows to push the retaining wire 4b first into the opening 22 in the longitudinal direction of the handle 2 and subsequently to bend it over following the hole 6, thus locking it there with the lock 5, whereby the opening 22 opens into the hole 6.

In both embodiments in the region of its face, the handle 2 is protruding past that portion of the hole 6 which is provided in it. This overlap 25 forms a stop for the rotating or pivoting lock 5 in its closed position, so that precisely defined position of the closed position of the lock 5 is given and thus the size of the divided hole 6 is also determined and cannot vary due to possible different pivoted positions of the lock 5.

On the same occasion in this embodiment it is provided both for the retention of the hard brush 4 and of the fine brush 3 that in the locked position the lock 5 engages the overlap 25 on the face of the handle 2, which overlap serves as a stop, and in this engaged region it provides a guidance, lock, detachable clamping connection or a similar retention, which can be constructed analogously to the corresponding retention according to FIGS. 2 to 11, while in this case each can have engaging means or retaining devices 12 corresponding to the slat-shaped parts 23 and 24.

As in the embodiment according to FIGS. 1 to 12i, in this case too in the closed position the lock 5 may have a detachable snap-in or clip-in connection with a contact position of the handle, e.g., on the face, thus preventing an unintentional opening during use.

The teeth-cleaning device 1 with a handle 2 has at one, or preferably at two opposite ends an interdental treatment element in the form of, for example, a fine brush 3 or a hard brush 4, possibly also of a toothpick. At the same time this treatment element is provided protruding transversely to the longitudinal extension of the handle 2 and fastened in a detachable and exchangeable manner, while the fastening is carried out by means of a lock 5 which can be fixed detachably in the locked position. For this purpose the treatment element or a retaining device associated with it, for example a retaining wire 4a, inserted in the operating position into a hole 6 extending transversely to the longitudinal extension of the handle 2, and when the lock 5 exposes this hole 6, the treatment element can be removed again and replaced by another one. In contrast to this, in the closed position the lock 5 overlaps the hole 6 and thus prevents the removal of the treatment element inserted into it. At the same time the lock 5 has a slat-shaped design and is provided and fitted into a recess 7 or a cross-section reduction of the handle 2 in such a manner that, as far as the cross-section is concerned, in the locked and operating position it is a flush or protrusion-free component of the handle 2. The lock 5 has a rotary mounting 8 at a distance from the hole 6, the axis A of which extends parallel to the longitudinal axis and the direction of insertion of the respective treatment element. Therefore the lock 5 has a turn handle-like design and can be brought into a position which is perpendicular to the handle 2 and the recess 7, in which position the hole 6 is exposed. When the lock is brought again into alignment with the handle 2, it will be flush with it and will simultaneously close off the hole 6, therefore locking the removal of the treatment element and fixing it. On the same occasion the hole 6 also may be provided partly in the handle, partly in the lock itself, i.e., complementing itself in the closed position of the lock thus forming the actual hole.

It will be appreciated by those skilled in the art that changes could be made to the embodiment(s) described above without departing from the broad inventive concept thereof. It is understood, therefore, that this invention is not limited to the particular embodiment(s) disclosed, but it is intended to cover modifications within the spirit and scope of the present invention as defined by the appended claims.

We claim:

1. A teeth-cleaning device comprising:
    a handle having a longitudinal extension having a first side, a second side opposite the first side, and a hole extending transversely to the handle, the first side having a recess having a flat portion extending past the hole;
    at least one detachable and exchangeable interdental treatment element having a longitudinal axis, the interdental treatment element being provided on the second side of the longitudinal extension and protruding transversely to the longitudinal extension;
    a retaining device associated with the interdental treatment element; and
    a slat-shaped-like lock having a locked position and an unlocked position, the lock having a flat and level side facing the flat portion of the recess and being associated via a rotary mounting with the recess in such a manner that in the locked position the lock is a substantially protrusion-free component of the handle, the rotary mounting being at a distance to the hole in the longitudinal extension and having an axis extending parallel to the longitudinal axis of the treatment element;
    wherein with the lock in the unlocked position, the lock exposes a cross-section of the hole and one of the treatment element and the retaining device is insertable into the hole; and
    wherein with the lock in the locked position, the lock overlaps the hole and prevents removal of the one of the treatment element and retaining device from the hole.

2. A teeth-cleaning device comprising:
    a handle having a terminal end and a longitudinal extension having a hole extending transversely to the longitudinal extension and a recess;
    at least one detachable and exchangeable interdental treatment element having a longitudinal axis, the interdental treatment element being provided on the longitudinal extension and protruding transversely to the longitudinal extension;
    a retaining device associated with the interdental treatment element; and
    a slat-shaped-like lock having a locked position and an unlocked position, the lock being associated via a rotary mounting with the recess of the handle in such a manner that in the locked position the lock is a substantially protrusion-free component of the handle, the rotary mounting being at a distance to the hole in the longitudinal extension and having an axis extending parallel to the longitudinal axis of the treatment element, the hole (6) for accommodating and retaining the treatment element being closer to the terminal end of the handle (2) than the rotary mounting (8) of the lock (5);
    wherein with the lock in the unlocked position the lock exposes a cross-section of the hole and one of the treatment element and the retaining device is insertable into the hole; and
    wherein with the lock in the locked position, the lock overlaps the hole and prevents removal of the one of the treatment element and retaining device from the hole.

3. A teeth-cleaning device comprising:
    a handle having a longitudinal extension having a hole extending transversely to the longitudinal extension and a recess having a shoulder bounding the recess;
    at least one detachable and exchangeable interdental treatment element having a longitudinal axis, the interdental treatment element being provided on the longitudinal extension and protruding transversely to the longitudinal extension,
    a retaining device associated with the interdental treatment element; and
    a slat-shaped-like lock having a locked position and an unlocked position the lock being associated via a rotary mounting with the recess in such a manner that in the locked position the lock is a substantially protrusion-free component of the handle, the rotary mounting being at a distance to the hole in the longitudinal extension and having an axis (A) extending parallel to the longitudinal axis of the treatment element, the lock (5) further having a first arm and a second arm, the first and second arms extending in opposite directions from the rotary mounting (8), the first arm engaging the hole (6) when the lock is in the locked position and the second arm extending from the rotary mounting (8) in direction of the handle (2) up to the shoulder (9) bounding the recess (7);
    wherein with the lock in the unlocked position, the lock exposes a cross-section of the hole and one of the treatment element and the retaining device is insertable into the hole; and
    wherein with the lock in the locked position the lock overlaps the hole and prevents removal of the one of the treatment element and the retaining device from the hole.

4. The teeth-cleaning device according to claim 3, wherein the shoulder (9) between the handle (2) and the recess is provided approximately perpendicularly to a longitudinal extension and in the transverse direction has particularly a concave curvature, wherein a face (10) of the lock (5) facing the shoulder (9), when the lock is in the locked position, has a corresponding concave curvature, and wherein a radius of curvature of the concave curvature corresponds to a distance of the face (10) from the axis (A) of the rotary mounting (8).

5. The teeth-cleaning device according to claim 3, wherein the shoulder (9) and a face (10) of the lock are in contact when the lock is in the locked position.

6. The teeth-cleaning device according to claim 3, wherein a retaining means is provided on one of a face (10) of the lock (5) which faces the shoulder (9) and the shoulder (9) for a detachable fastening of the lock in the locked position.

7. The teeth-cleaning device according to claim 3, wherein the rotary mounting has a mushroom-shaped protrusion (15) provided on the lock and a counterpart recess (17) provided on the handle, the counterpart recess having one of a collar and a protrusion which snaps-in with the mushroom-shaped protrusion (15) and surrounds the mushroom shaped protrusion with one of the collar (16) and the protrusion.

8. A teeth-cleaning device comprising:
   a handle having a longitudinal extension having a hole extending transversely to the longitudinal extension and a recess;
   at least one detachable and exchangeable interdental treatment element having a longitudinal axis, the interdental treatment element being provided on the longitudinal extension and protruding transversely to the longitudinal extension;
   a retaining device associated with the interdental treatment element;
   a slat-shaped-like lock having a locked position and an unlocked position, the lock being associated via a rotary mounting with the recess of the handle in such a manner that in the locked position the lock is a substantially protrusion-free component of the handle, the rotary mounting being at a distance to the hole in the longitudinal extension and having an axis extending parallel to the longitudinal axis of the treatment element, the lock further having a face (11) facing the recess (7), the face having a protrusion provided for fixing of the lock (5) in the locked position; and
   wherein with the lock in the unlocked position, the lock exposes a cross-section of the hole and one of the treatment element and the retaining device is insertable into the hole; and
   wherein with the lock in the locked position, the lock overlaps the hole and prevents removal of the one of the treatment element and the retaining device from the hole.

9. A teeth-cleaning device comprising:
   a handle having a longitudinal extension having a hole extending transversely to the longitudinal extension and a recess, the handle further having an end face having an edge;
   at least one detachable and exchangeable interdental treatment element having a longitudinal axis, the interdental treatment element being provided on the longitudinal extension and protruding, transversely to the longitudinal extension:
   a retaining device associated with the interdental treatment element; and
   a slat-shaped-like lock having a locked position and an unlocked position, the lock being associated via a rotary mounting with the recess of the handle in such a manner that in the locked position the lock is a substantially protrusion-free component of the handle, the rotary mounting being at a distance to the hole in the longitudinal extension and having an axis extending parallel to the longitudinal axis of the treatment element, the lock further having a face having a protrusion; and
   a device to fix the lock in the locked position by means of frictional force, clamping force, form-locking or snapping-in, at least on one side of the lock;
   wherein with the lock in the unlocked position, the lock exposes a cross-section of the hole and one of the treatment element and the retaining device is insertable into the hole; and
   wherein with the lock in the locked position, the lock overlaps the hole and prevents removal of the treatment element and the retaining device from the hole and the protrusion (12) engages the edge of the end face of the handle.

10. A teeth-cleaning device comprising:
   a handle having a longitudinal extension having a hole extending transversely to the longitudinal extension and a recess;
   at least one detachable and exchangeable interdental treatment element having a longitudinal axis, the interdental treatment element being provided on the longitudinal extension and protruding transversely to the longitudinal extension;
   a retaining device associated with the interdental treatment element;
   a slat-shaped-like lock having a locked position and an unlocked position, the lock being associated via a rotary mounting with the recess of the handle in such a manner that in the locked position the lock is a substantially protrusion-free component of the handle, the rotary mounting being at a distance to the hole in the longitudinal extension and having an axis (A) extending parallel to the longitudinal axis of the treatment element; and
   wherein the at least one detachable and exchangeable interdental treatment element is at least a replaceable hard brush having bristles that are held by a central bendable retaining wire passable through the hole of the handle, the retaining wire protruding past the hole within reach of the lock, and can be bent relative to the hole by turning the lock into the locked position;
   wherein on a side (7a) of the recess (7) which faces the lock (5) a groove (8) is provided to accommodate the retaining wire (4a) the groove extending transversely to the longitudinal extension of the handle (2) and having an axis of curvature coinciding with the axis (A) of the rotary mounting (8), and wherein the hole (6) for the purpose of passing through the retaining wire (4a) opens into the groove (8);
   wherein with the lock in the unlocked position, the lock exposes a cross-section of the hole and one of the treatment element and the retaining device is insertable into the hole; and
   wherein with the lock in the locked position, the lock overlaps the hole and prevents removal of the one of the treatment element and the retaining device from the hole.

11. A teeth-cleaning device comprising:
a handle having a longitudinal extension having a hole extending transversely to the longitudinal extension and a recess;
at least one detachable and exchangeable interdental treatment element having a longitudinal axis, the interdental treatment element being provided on the longitudinal extension and protruding transversely to the longitudinal extension;
a retaining device associated with the interdental treatment element; and
a slat-shaped-like lock having a locked position and an unlocked position, the lock being associated via a rotary mounting with the recess of the handle in such a manner that in the locked position the lock is a substantially protrusion-free component of the handle, the rotary mounting being at a distance to the hole in the longitudinal extension and having an axis extending parallel to the longitudinal axis of the treatment element;
wherein the at least one detachable and exchangeable interdental treatment element is a fine brush-shaped treatment element (3), the retaining device is a retaining plate (3b), and the hole (6) has an entry region facing away from an exit and in the entry region a widening (19) which corresponds to the shape and the size of the retaining plate (3b), the brush-shaped treatment element having a treating end, a bundle of approximately parallel bristles (3a), an end of the treatment element (3) opposite to the treating end being secured to the retaining plate (3b), wherein a radial expansion of the retaining plate (3b) overlaps a cross-section of the bundle of bristles and the bundle of bristles is insertable through the hole (6), wherein upon the bundle of bristles being inserted through the hole (6), the hole (6) accommodates the retaining plate (3b) in a form-locking manner, and the retaining plate (3b) is approximately flush with an edge of the widening (19), and wherein in the locked position the lock (5) is close to a surface (20) of the retaining plate (3b);
wherein with the lock in the unlocked position, the lock exposes a cross-section of the hole and one of the treatment element and the retaining device is insertable into the hole; and
wherein with the lock in the locked position, the lock overlaps the hole and prevents removal of the one of the treatment element and the retaining device from the hole.

12. The teeth-cleaning device according to claim 11, wherein the retaining plate (3b) has an external contour and a plate-shaped, longitudinal tapering section, which fits the correspondingly shaped widening (19) of the retaining hole (6) of the handle (2) and is held therein in an axial direction.

13. The teeth-cleaning device according claim 11, wherein the fine brush-shaped treatment element is a soft brush-shaped treatment element wherein a separating plane of the hole (6) to accommodate the soft brush (3) corresponds to a longitudinal central plane through the rotary mounting (8) and the hole (6) when the lock is in the locked position.

14. A teeth-cleaning device comprising:
a handle having a first longitudinal extension at one end region having a first hole extending transversely to the extension and a first reduced cross-section and a second longitudinal extension at the other end region having a second hole extending transversely to the extension and a second reduced cross-section;
a first and a second detachable and exchangeable interdental treatment element having a longitudinal axis, the first interdental treatment element being provided on the first longitudinal extension and protruding transversely to the first longitudinal extension and the second interdental treatment element being provided on the second longitudinal extension and protruding transversely to the second longitudinal extension;
a first and a second retaining device respectively associated with the first and second interdental treatment elements; and
a first slat-shaped-like lock having a locked position and an unlocked position, the first lock being associated via a first rotary mounting with the reduced cross-section of the first longitudinal extension in such a manner that in the locked position the first lock is a substantially protrusion-free component of the longitudinal extension, the first rotary mounting being at a distance to the first hole in the first longitudinal extension and having an axis extending parallel to the longitudinal axis of the first treatment element;
a second slat-shaped-like lock having a locked position and an unlocked position, the second lock being associated via a second rotary mounting with the reduced cross-section of the second longitudinal extension in such a manner that in the locked position the second lock is a substantially protrusion-free component of the longitudinal extension, the second rotary mounting being at a distance to the second hole in the second longitudinal extension and having an axis extending parallel to the longitudinal axis of the second treatment element;
wherein with the first lock in the unlocked position, the first lock exposes a cross-section of the first hole and one of the first treatment element and the first retaining device is insertable into the first hole and with the second lock in the unlocked position, the second lock exposes a cross-section of the second hole and one of the second treatment element and the second retaining device is insertable into the second hole; and
wherein with the first lock in the locked position, the first lock overlaps the first hole and prevents removal of the one of the first treatment element and the first retaining device from the first hole and with the second lock in the locked position, the second lock overlaps the second hole and prevents removal of the one of the second treatment element and the second retaining device from the second hole.

15. The teeth-cleaning device according to claim 14, wherein the first and second treatment elements protrude on opposite situated ends of the handle (2) in opposite situated sides from the handle (2).

16. The teeth-cleaning device according to claim 14, wherein at the one end region a pointed fine brush (3) formed from a bundle of bristles is provided, and at the other end region a hard brush (4) with a retaining wire (4a) and bristles (4b) protruding from the retaining wire is provided.

17. A teeth-cleaning device comprising:
a handle having a longitudinal extension having a hole extending transversely to the longitudinal extension and a recess;
at least one detachable and exchangeable interdental treatment element having a longitudinal axis, the interdental treatment element being provided on the longitudinal extension and protruding transversely to the longitudinal extension;

a retaining device associated with the interdental treatment element; and a slat-shaped-like lock having a locked position and an unlocked position the lock being associated via a rotary mounting with the recess of the handle in such a manner that in the locked position the lock is a substantially protrusion-free component of the handle, the rotary mounting being at a distance to the hole in the longitudinal extension and having an axis extending parallel to the longitudinal axis of the treatment element;

wherein with the lock in the unlocked position, the lock exposes a cross-section of the hole and one of the treatment element and the retaining device is insertable into the hole; and wherein with the lock in the locked position, the lock overlaps the hole and prevents removal of the one of the treatment element and the retaining device from the hole; and wherein a length of the hole (6) is divided for the treatment element in such a manner that one portion of an internal wall of the hole (6) is provided on the handle (2), and another portion of the internal wall complementing the one portion with the lock in the locked position is provided on a portion of the lock (5), which leg extends approximately parallel to the axis of rotation (A) of the lock (5), and wherein in the case of the lock (5) being in the unlocked position, for the purpose of inserting the treatment element or the retaining device associated with the treating element, the hole (6) is divided and exposed, and after pivoting or rotating the lock (5) into the locked position the internal wall surrounds the one of the treatment element and the retaining device of the treatment element.

18. The teeth-cleaning device according to claim 17, wherein the divided hole (6) has a widening (19) extending in a direction of the rotary mounting (8) of the lock (5).

19. The teeth-cleaning device according to claim 17, wherein the handle has at least two recesses and the lock (5) has two, approximately slat-shaped parts (23,24) which are parallel to each other, which are rotatably mounted on parallel flats (7a) of the recesses (7) of the handle (2), wherein a region (21) of the lock (5) containing a portion of the hole (6) joins both slat-shaped portions (23,24), and wherein the entire lock (5) has an approximately U-shaped longitudinal section, whereby the two slat-shaped portions (23,24) form legs of the U and contain the rotary mounting (8).

20. The teeth-cleaning device according to claim 17, wherein a part of the hole (6) which is part of the handle (2) is arranged on a face of the handle (2) in such a manner that when the lock (5) is in the locked position a center of the hole is in a longitudinal central plane of the rotary mounting (8) of the lock (5).

21. The teeth-cleaning device according to claim 17, wherein the treatment element is a replaceable hard brush (4) with a central retaining wire (4b) wherein a part of the hole (6) which is arranged on a face of the handle (2) extends on both sides of a longitudinal central plane and is open on another face facing away from the central plane and extends over more than half of the cross-section of the hole, and an other portion of the hole which is situated in the lock (5) is open over the entire length of the other portion in a direction of rotation and also extends over more than half of the cross-section of the hole.

22. A teeth-cleaning device comprising:

a handle having a longitudinal extension having a hole extending transversely to the longitudinal extension and a recess;

at least one detachable and exchangeable interdental treatment element having a longitudinal axis, the interdental treatment element being provided on the longitudinal extension and protruding transversely to the longitudinal extension;

a retaining device associated with the interdental treatment element; and a slat-shaped-like lock having a locked position and an unlocked position, the lock being associated via a rotary mounting with the recess of the handle in such a manner that in the locked position the lock is a substantially protrusion-free component of the handle, the rotary mounting being at a distance to the hole in the longitudinal extension and having an axis extending parallel to the longitudinal axis of the treatment element;

wherein the handle further has an overlap in a region of a face of the handle (2) that overlaps a portion of the hole (6) which is provided in the handle, and the overlap (25) forms a stop for the rotating lock (5) in locked position;

wherein with the lock in the unlocked position, the lock exposes a cross-section of the hole and one of the treatment element and the retaining device is insertable into the hole; and wherein with the lock in the locked position, the lock overlaps the hole and prevents removal of the one of the treatment elements and the retaining device from the hole.

23. The teeth-cleaning device according to claim 22, wherein in the locked position the lock (5) engages the overlap (25) on the face of the handle (2), which overlap serves as a stop, and in a region of engagement, the lock provides a detachable clamping connection.

24. A teeth-cleaning device comprisin:

a handle having a longitudinal extension having a hole extending transversely to the longitudinal extension and a recess;

at least one detachable and exchangeable interdental treatment element having a longitudinal axis, the interdental treatment element being provided on the longitudinal extension and protruding transversely to the longitudinal extension;

a retaining device associated with the interdental treatment element; and a slat-shaped-like lock having a locked position and an unlocked position, the lock being associated via a rotary mounting with the recess of the handle in such a manner that in the locked position the lock is a substantially protrusion-free component of the handle, the rotary mounting being at a distance to the hole in the longitudinal extension and having an axis extending parallel to the longitudinal axis of the treatment element;

wherein with the lock in the unlocked position, the lock exposes a cross-section of the hole and one of the treatment element and the retaining device is insertable into the hole; and wherein with the lock in the locked position, the lock overlaps the hole and prevents removal of the one of the treatment element and the retaining device from the hole and the lock (5) has a detachable clip-in connection with a contact position of the handle.

* * * * *